(12) United States Patent
Lee

(10) Patent No.: US 11,376,070 B2
(45) Date of Patent: Jul. 5, 2022

(54) MEDICAL LASER DEVICE

(71) Applicant: LUTRONIC CORPORATION, Goyang-si (KR)

(72) Inventor: Hee Chul Lee, Goyang-si (KR)

(73) Assignee: LUTRONIC CORPORATION

( * ) Notice: Subject to any disclaimer, the term of this patent is extended or adjusted under 35 U.S.C. 154(b) by 67 days.

(21) Appl. No.: 16/770,307

(22) PCT Filed: Nov. 7, 2018

(86) PCT No.: PCT/KR2018/013421
§ 371 (c)(1),
(2) Date: Jun. 5, 2020

(87) PCT Pub. No.: WO2019/112189
PCT Pub. Date: Jun. 13, 2019

(65) Prior Publication Data
US 2021/0169573 A1 Jun. 10, 2021

(30) Foreign Application Priority Data

Dec. 8, 2017 (KR) .......................... 10-2017-0168481

(51) Int. Cl.
*A61B 18/20* (2006.01)
*A61B 18/00* (2006.01)
(Continued)

(52) U.S. Cl.
CPC ... *A61B 18/203* (2013.01); *A61B 2017/00115* (2013.01); *A61B 2018/00452* (2013.01);
(Continued)

(58) Field of Classification Search
CPC ........ A61B 18/203; A61B 2017/00115; A61B 2018/00452; A61B 2018/00666;
(Continued)

(56) References Cited

U.S. PATENT DOCUMENTS

2010/0185121 A1* 7/2010 Carroll ..................... A61B 5/03
600/587
2011/0245833 A1* 10/2011 Anderson ........... B25B 23/0064
606/80

(Continued)

FOREIGN PATENT DOCUMENTS

JP  2005224502   8/2005
JP  2006288965   10/2006

(Continued)

OTHER PUBLICATIONS

International Search Report; International Application No. PCT/KR2018/013421 dated Feb. 7, 2019.

*Primary Examiner* — Brian T Gedeon
*Assistant Examiner* — Joshua Andrew Schum-Houck
(74) *Attorney, Agent, or Firm* — Perman & Green, LLP

(57) ABSTRACT

A medical handpiece having a laser irradiation unit connected to a body for generating a laser beam, so as to irradiate a subject with the laser beam; a laser tip which is brought into contact with a predetermined surgical site of the subject so as to guide the laser thereto; a sensor installed in the laser tip so as to measure pressure applied by the laser tip to the predetermined surgical site; and a processor for checking whether the measured pressure is within the pressure range set for the predetermined surgical site, determining, according to the result of the checking, whether the pressure applied to the predetermined surgical site needs to be adjusted, and performing control such that a guide signal for the laser tip is output.

12 Claims, 10 Drawing Sheets

(51) Int. Cl.
*A61B 90/00* (2016.01)
*A61B 17/00* (2006.01)

(52) U.S. Cl.
CPC ............ *A61B 2018/00666* (2013.01); *A61B 2090/065* (2016.02); *A61B 2562/0247* (2013.01); *A61B 2562/164* (2013.01)

(58) Field of Classification Search
CPC ...... A61B 2090/065; A61B 2562/0247; A61B 2562/164; A61B 18/201; A61B 2017/00119; A61B 2018/0066; A61B 2018/00672; A61B 2018/00678; A61B 2018/00922; A61B 2018/205547; A61B 18/20; A61B 2018/00636; A61N 5/0616; A61N 2005/0626; A61N 2005/0664; A61N 5/067
See application file for complete search history.

(56) References Cited

U.S. PATENT DOCUMENTS

2011/0295160 A1* 12/2011 Hart .................. B25D 9/08
 601/2
2015/0148615 A1* 5/2015 Brennan ................ A61B 50/33
 600/249

FOREIGN PATENT DOCUMENTS

| KR | 1020130006109 | 1/2013 |
|----|---------------|--------|
| KR | 1020140047287 | 4/2014 |
| KR | 1020160099332 | 8/2016 |
| KR | 2020160002847 | 8/2016 |

* cited by examiner

510

520

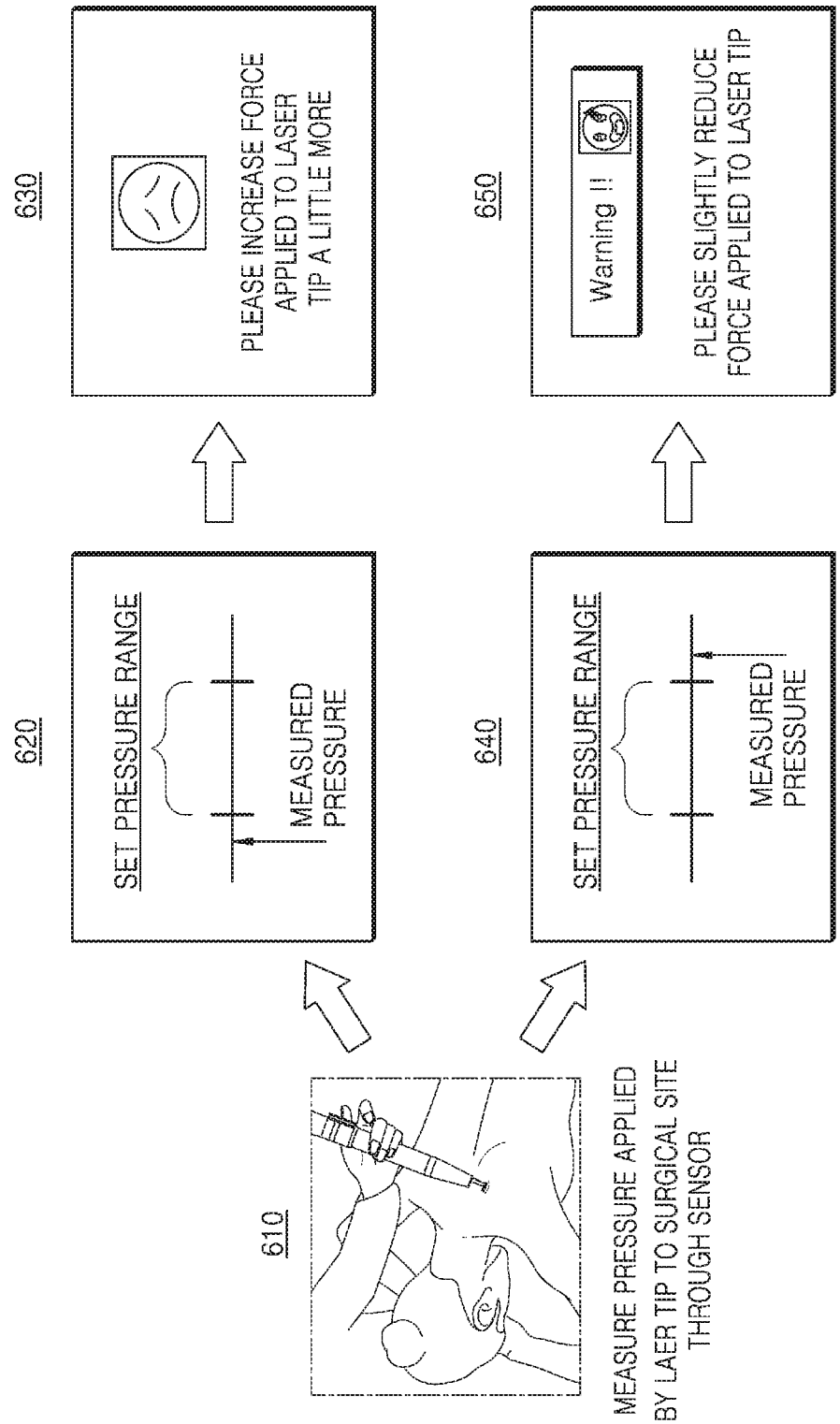

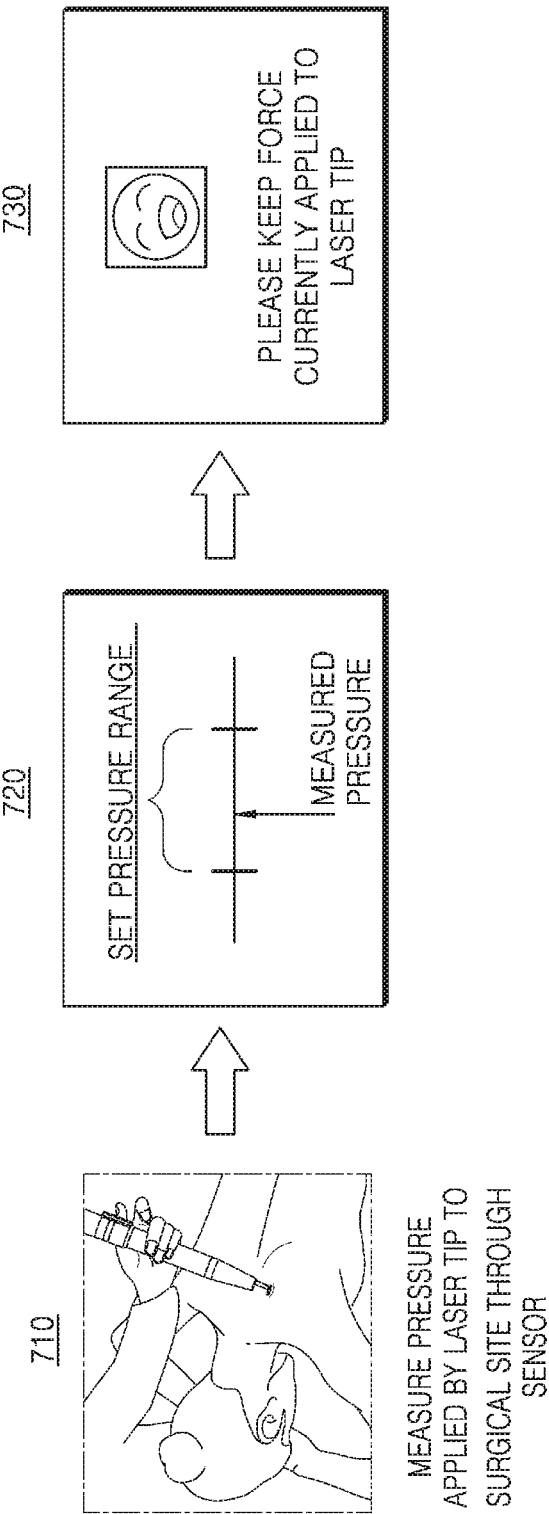

MEDICAL LASER DEVICE

CROSS REFERENCE TO RELATED APPLICATIONS

This application is a National Stage of International Application No. PCT/KR2018/013421, having an International Filing Date of 7 Nov. 2018, which designated the United States of America, and which International Application was published under PCT Article 21(2) as WO Publication No. 2019/112189 A1, which claims priority from and the benefit of Korean Patent Application No. 10-2017-0168481, filed on 8 Dec. 2017, the disclosures of which are incorporated herein by reference in their entireties.

BACKGROUND

1. Field

The present disclosure relates to a medical laser device.

2. Brief Description of Related Developments

Lasers are used in various fields such as industrial, medical, and military applications. In particular, medical laser devices are used in ophthalmology, density, surgery, and dermatology. For example, medical laser devices are used to treat a lesion by irradiating a lesion such as a skin disease or vascular disease occurring on the skin with a laser beam.

When the skin surface or lesion is irradiated with the laser beam, molecules constituting the skin tissues vibrate and rub against each other whenever the current direction of the laser beam changes. Thus, deep heat is generated by a rotational motion, warping, or a collision motion. Deep heat can increase the temperature of the skin tissues and reorganize the collagen layer to improve wrinkles and strengthen skin elasticity.

However, when the skin surface or lesion is irradiated with the laser beam in a state in which the skin surface or lesion is severely pressed or away from the skin surface or lesion, the treatment or treatment effect cannot be increased. Therefore, a medical laser device that irradiates a laser beam while applying an optimal pressure to the skin surface or lesion, is required.

SUMMARY

A medical laser device may induce an optimal pressure to be applied to a predetermined surgical site of a subject by using a sensor installed in a laser tip.

In particular, when the pressure measured by the sensor is out of a pressure range set for the predetermined surgical site, the medial laser device may generate and output a guide signal that induces the pressure applied by the laser tip to have a pressure within a predetermined pressure range.

According to an aspect of the present disclosure, a medical handpiece includes a laser irradiation unit connected to a body for generating a laser, so as to irradiate a subject with the laser, a laser tip which is brought into contact with a predetermined surgical site of the subject so as to guide the laser thereto, a sensor installed in the laser tip so as to measure pressure applied by the laser tip to the predetermined surgical site, and a processor for checking whether the measured pressure is within the pressure range set for the predetermined surgical site, determining, according to the result of the checking, whether the pressure applied to the predetermined surgical site needs to be adjusted, and performing control such that a guide signal for the laser tip is output.

According to another aspect of the present disclosure, a medical laser device includes a body for generating a laser, a handpiece connected to the body, so as to irradiate the laser, a sensor installed in a laser tip within the handpiece and measuring the pressure applied to a predetermined surgical site of a subject, and a processor for checking whether the measured pressure is within the pressure range set for the predetermined surgical site, determining, according to the result of the checking, whether the pressure applied to the predetermined surgical site needs to be adjusted, and performing control such that a guide signal for the laser tip is output.

According to another aspect of the present disclosure, a computer-readable storage medium on which commands that can be executed by a processor are stored, includes a command for measuring the pressure applied by a laser tip to a predetermined surgical site of a subject through a sensor installed in the laser tip within a handpiece, a command for checking whether the measured pressure is within a pressure range set for the predetermined surgical site, and a command for determining, according to the result of the checking, whether the pressure applied to the predetermined surgical site needs to be adjusted, and performing control so that a guide signal for the laser tip is output.

When the pressure measured by a sensor is out of a pressure range set for a predetermined surgical site, a medical laser device may generate and output a guide signal that induces the pressure applied by a laser tip to have a pressure within a predetermined pressure range, so that the optimal pressure can be induced to be applied to a predetermined surgical site of a subject.

BRIEF DESCRIPTION OF THE DRAWINGS

The present disclosure can be easily understood by a combination of the following detailed description and accompanying drawings, and reference numerals refer to structural elements.

FIG. 6 is a view for explaining a process of displaying guide information corresponding to a guide signal in a medical laser device when the pressure measured by the sensor is out of a set pressure range, according to an aspect.

FIG. 7 is a view for explaining a process of displaying guide information corresponding to a guide signal in a medical laser device when the pressure measured by the sensor is within a set pressure range, according to an aspect.

A medical handpiece may include a laser irradiation unit connected to a body for generating a laser, so as to irradiate a subject with the laser, a laser tip which is brought into contact with a predetermined surgical site of the subject so as to guide the laser thereto, a sensor installed in the laser tip so as to measure pressure applied by the laser tip to the predetermined surgical site, and a processor for checking whether the measured pressure is within the pressure range set for the predetermined surgical site, determining, according to the result of the checking, whether the pressure applied to the predetermined surgical site needs to be adjusted, and performing control such that a guide signal for the laser tip is output.

A medical laser device may include a body for generating a laser, a handpiece connected to the body, so as to irradiate the laser, a sensor installed in a laser tip within the handpiece and measuring the pressure applied to a predetermined surgical site of a subject, and a processor for checking whether the measured pressure is within the pressure range set for the predetermined surgical site, determining, according to the result of the checking, whether the pressure applied to the predetermined surgical site needs to be adjusted, and performing control such that a guide signal for the laser tip is output.

DETAILED DESCRIPTION

The terminology used in the present disclosure has been selected, while considering the functions in the present disclosure, general terms that are currently widely used are selected, but this may vary according to the intention or precedent of a person skilled in the art or the appearance of a new technology. In addition, in certain cases, some terms are arbitrarily selected by the applicant, and in this case, their meanings will be described in detail in the description of the present disclosure. Therefore, the terms used in the present disclosure should be defined based on the meanings of the terms and the contents of the present disclosure, not simply the names of the terms.

It will be understood that, when a portion "comprises" a certain component throughout the specification, this means that a portion may further comprise other components instead of excluding other components, unless specifically stated to the contrary.

Hereinafter, aspects of the present disclosure will be described in detail with reference to the accompanying drawings so that those skilled in the art to which the present disclosure pertains, may easily practice. However, the present disclosure can be embodied in many different forms and is not limited to the aspects described herein.

Hereinafter, the aspects will be described in detail with reference to the drawings.

Figure 1:
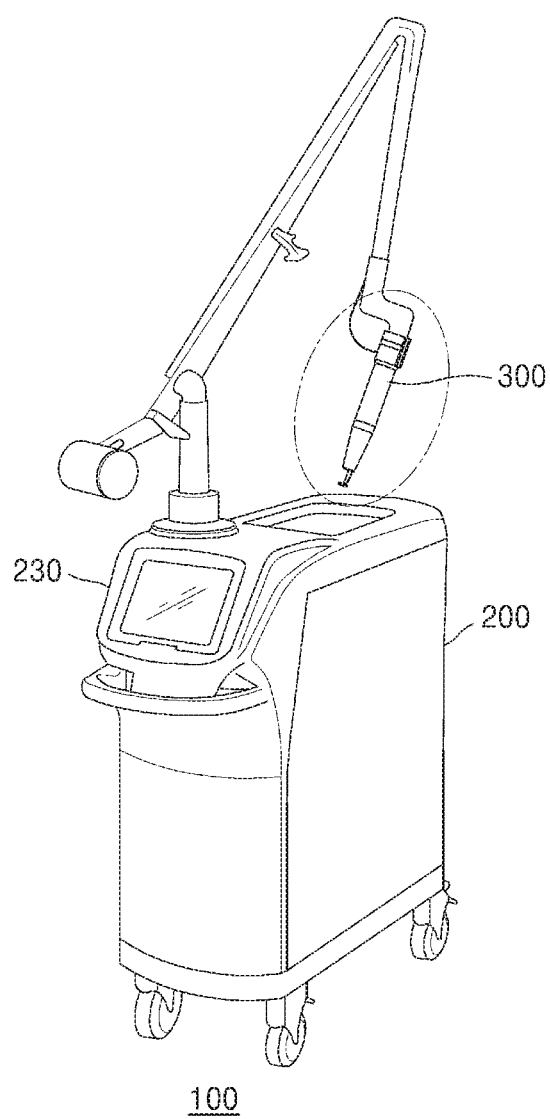
FIG. 1 is a view illustrating the appearance of a medical laser device according to an aspect.

FIG. 1 is a view illustrating the appearance of a medical laser device according to an aspect.

A medical laser device 100 may include a body 200 and a handpiece 300. The medical laser device 100 may be used to perform a medical procedure or treatment on a predetermined region of a subject (for example, uterus, jaw, lesion, etc.).

A power supply unit (not shown) for receiving power from the outside may be provided inside the body 200. A laser oscillation unit that generates a treatment laser (hereinafter, referred to as a 'laser') to be irradiated onto the skin of the subject by using power supplied by a power supply unit (not shown) may be provided inside the body 200. In addition, a processor for controlling the medical laser device 100 or components of the medical laser device 100 may be provided inside the body 200.

In addition, a control panel for manipulating the driving content of a medical treatment device and a display 230 for displaying an image related to the driving content or surgical site of the medical treatment device may be provided outside the body 200.

The body 200 and the handpiece 300 may be connected to each other via a connection unit. The connection unit may have a shape of a link in which the position of the handpiece 300 may be adjusted by a user who holds the handpiece 300.

In addition, the handpiece 300 connected to the body 200 may be replaced with another handpiece 300 according to a surgical site or procedure. For example, the handpiece 300 may be replaced by varying the shape or size of a laser tip according to the surgical site or procedure.

The handpiece 300 may be connected to the body 200, may be held by the user to be moved to a predetermined surgical site of a subject requiring laser irradiation. The handpiece 300 may irradiate the predetermined surgical site of the subject with a laser provided by the laser oscillation unit of the body 200.

The handpiece 300 may be held by the user so that the laser emitted from the laser irradiation unit may be incident through a refraction arm and the incident laser may be irradiated onto a predetermined surgical site in the skin of the subject. In addition, the handpiece 300 may convert a laser of a first wavelength generated by the laser oscillation unit to a laser of a second wavelength and output the laser. In addition, the handpiece 300 may include a filter that transmits only light of the laser of the second wavelength.

Figure 2:
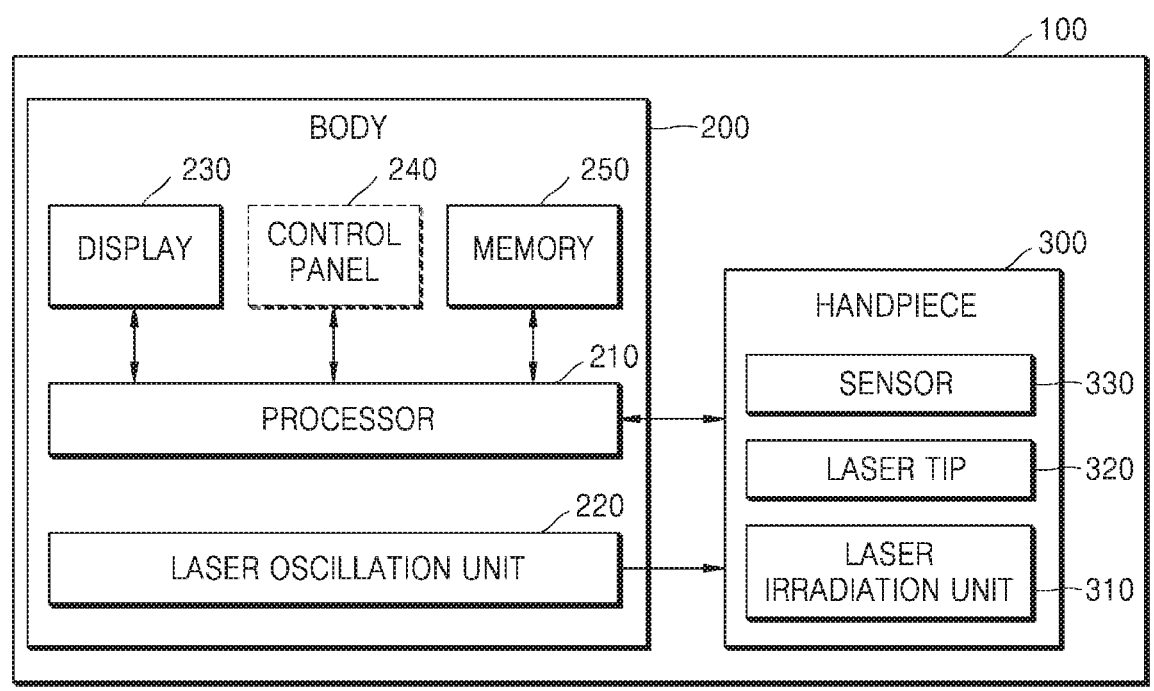
FIG. 2 is a block diagram illustrating the configuration of a medical laser device according to an aspect.

FIG. 2 is a block diagram illustrating the configuration of a medical laser device according to an aspect.

A medical laser device 100 may include a body 200 and a handpiece 300. The body 200 may include a processor 210, a laser oscillation unit 220, a display 230, a control panel 240, and memory 250. The handpiece 300 may include a laser irradiation unit 310, a laser tip 320, and a sensor 330. In addition, the body 200 and the handpiece 300 may be connected to each other via a cable (not shown). Not all of the components shown are essential. The medical laser device 100 may be implemented by more components than the illustrated components, and the medical laser device 100 may also be implemented by fewer components. Hereinafter, the components described above will be described.

The processor 210 of the body 200 may control an overall operation of the medical laser device 100 and the signal flow between internal components of the medical laser device 100. In addition, the processor 210 of the body 200 may include memory for storing a program or data for performing the function of medical laser device 100, or a processor 210 for processing the program or the data. In addition, the processor 210 of the body 200 may receive a control signal from the control panel 240 or a manipulation unit of the handpiece 300 so as to control an operation of the medical laser device 100.

The laser oscillation unit 220 may generate a laser to be irradiated onto a predetermined surgical site of the subject.

The display 230 may display an image related to the driving content of the medical laser device 100 or the surgical site. For example, the display 230 may display information related to an operating mode operated by the medical laser device 100 or a sensing signal sensed by the sensor. In addition, the display 230 may be combined with a touch panel and may also be implemented with a touch screen.

The control panel 240 may receive an input for manipulating the driving content of the medical laser device 100. The control panel 240 may be implemented with a button, a track ball, a jog switch, a knop, etc., and embodiments of the present disclosure are not limited thereto. When the operating mode of the medical laser device 100 is set through the control panel 240, information about the set operating mode may be transmitted to the processor 210 of the body 200. The processor 210 of the body 200 may control the laser oscillation unit 220 so as to generate a laser corresponding to the set operating mode.

The handpiece 300 may be connected to the body 200 via a cable (not shown). The cable (not shown) may include a laser transmitting unit (not shown) and a signal line (not shown). The laser transmitting unit (not shown) may electrically connect the laser oscillation unit 220 of the body 200 to an electrode portion of the handpiece 300 and thus may be formed as a circuit capable of providing a laser beam to a predetermined surgical site, and aspect of the present disclosure are not limited thereto. Through a signal line (not shown), various control signals or sensing signals may be transmitted/received between the body 200 and the handpiece 300.

For example, through the signal line (not shown), a control signal manipulated by the user through the manipulation unit of the handpiece 300, a signal sensed by the sensor 330 of the handpiece 300, and data may be transmitted to the processor 210 of the body 200. In addition, a control signal for controlling the operation of the handpiece 300 by using the processor 210 of the body 200 may be transmitted to the handpiece 300 through the signal line (not shown).

The handpiece 300 may be connected to the body 200 and may irradiate the subject with the laser generated in the body 200. The handpiece 300 may include the laser tip 320 that is brought into contact with a predetermined surgical site of the subject so as to guide the laser thereto. The sensor 330 may be installed in the laser tip 320 and may measure the pressure applied by the laser tip 320 to the predetermined surgical site. The handpiece 300 may transmit an input signal obtained by the sensor 330 to the processor 210 of the body 200 through the signal line (not shown).

The processor 210 of the body 200 may check whether the measured pressure is within a pressure range set for the predetermined surgical site. The processor 210 of the body 200 may determine whether the pressure applied to the predetermined surgical site needs to be adjusted, according to the result of checking, and may perform control such that a guide signal for the laser tip 320 may be output.

Here, the "guide signal" may be a signal that induces a pressure within a predetermined pressure range to be applied to a predetermined surgical site. In addition, the predetermined "pressure range" may mean the range of the pressure to be applied to the predetermined surgical site so as to maximize the effect of treatment while a laser beam is irradiated onto a predetermined surgical site and treatment is performed. In addition, since the direction of blood vessels and elasticity of the skin are different for sites of the subject, the predetermined "pressure range" for each of the sites of the subject may be set differently.

In detail, if it is checked that the measured pressure is out of the pressure range set for the predetermined surgical site, the processor 210 of the body 200 may generate a guide signal on the basis of information about the measured pressure being out of the pressure range, and may perform control so that the guide signal may be output.

For example, if it is checked that the size of the measured pressure is less than the size of a minimum pressure in the set pressure range, the processor 210 of the body 200 may perform control so that a first sound signal may be output through a speaker (not shown). After the first sound signal is output, as the pressure measured at the predetermined surgical site approaches the set pressure range, the processor 210 of the body 200 may perform control so that the magnitude of the first sound signal may be gradually decreased and the first sound signal may be output through the speaker (not shown).

In another example, if it is checked that the size of the measured pressure is greater than the size of the maximum pressure in the set pressure range, the processor 210 of the body 200 may perform control so that the second sound signal may be output through the speaker (not shown). After the second sound signal is output, as the pressure measured at the predetermined surgical site is away from the set pressure range, the processor 210 of the body 200 may perform control so that the magnitude of the second sound signal may be gradually increased and output through the speaker (not shown).

On the other hand, the display 230 may display an execution screen for controlling an operation of the medical laser apparatus 100 or an image related to a predetermined surgical site. The processor 210 of the body 200 may generate a guide signal for the laser tip on the basis of the pressure information measured by the sensor 330 and the pressure range set for the predetermined surgical site. The processor 210 of the body 200 may perform control so that guide information corresponding to the generated guide signal for the laser tip 320 may be displayed on the display 230.

For example, when the pressure measured by the sensor 330 is out of the pressure range set for the predetermined surgical site, the display 230 may display the measured pressure and a value of the pressure range set for the predetermined surgical site. In addition, the display 230 may also visualize (for example, pictures, symbols, tables, etc.) the measured pressure and the pressure range set for the predetermined surgical site. In addition, the display 230 may display guide information that induces the pressure to be applied to the predetermined surgical site within the range of the pressure to be applied to the surgical site. In addition, the display 230 may perform control so that a degree at which the measured pressure is out of the pressure range for the predetermined surgical site, may be displayed on the display 230 on the basis of the guide signal.

The memory 250 may store information in which a predetermined pressure range corresponding to a plurality of sites of the subject is set for each of the plurality of sites of the subject. In addition, the memory 250 may store a computer program that performs a method of outputting a guide signal for the laser tip 320 by using the pressure measured at the predetermined surgical site.

Here, the memory 250 may include at least one type storage medium from among a flash memory type, a hard disk type, a multimedia card micro type, card type memory (secure digital (SD), extreme digital (XD) memory, etc.), random access memory (RAM), static random access memory (SRAM), read-only memory (ROM), electrically erasable programmable read-only memory (EEPROM), programmable read-only memory (PROM), magnetic memory, a magnetic disk, and an optical disk.

When the display 230 is combined with the touch panel and is implemented with a touch screen, the display 230 may display an execution screen for controlling the operation of the medical laser device 100. The display 230 may receive an input for selecting a first site from among the plurality of sites through the execution screen. The processor 210 of the body 200 may determine whether the pressure needs to be adjusted for the first site, on the basis of the pressure measured by the sensor 330, and may generate a guide signal for the laser tip 320. The processor 210 of the body 200 may perform control so that guide information corresponding to the generated guide signal may be displayed on the display 230. In addition, the processor 210 of the body 200 may perform control so that a sound signal corresponding to the generated guide signal may be output through the speaker.

On the other hand, the sensor 330 may be a film-type sensor. For example, the sensor 330 may be a pressure sensor made of a transparent thin-film material, and aspects of the present disclosure are not limited thereto. Here, the pressure sensor may be an electrical pressure sensor, such as a strain gauge type, a capacitive type, a piezoelectric type, an inductance type, a semiconductor type force sensitive resistor (FSR), and the like. In addition, the sensor 330 may be installed at an end of the laser tip 320.

In addition, the sensor 330 may include a plurality of sub-sensors. The plurality of sub-sensors may be arranged and installed at an end of the laser tip 320 that is brought into contact with the predetermined surgical site at predetermined intervals. The laser tip 320 may induce a tension with a predetermined size to the predetermined surgical site while pressing the predetermined surgical site. The plurality of sub-sensors may be in contact with the predetermined surgical site so as to measure the tension induced to the predetermined surgical site.

The medical laser device 100 may induce an optimal pressure to be applied to the predetermined surgical site of the subject by using the sensor 330 installed in the laser tip 320.

In particular, if the pressure measured by the sensor 330 is out of the pressure range set for the predetermined surgical site, the medical laser device 100 may generate a guide signal that induces the pressure applied by the laser tip 320 to have the pressure within a predetermined pressure range, and may output the guide signal.

In addition, the medical laser device 100 may perform control so that a laser may be irradiated to a predetermined surgical site within a predetermined pressure range. Thus, the laser beam may be focused on the dermis.

Figure 3:
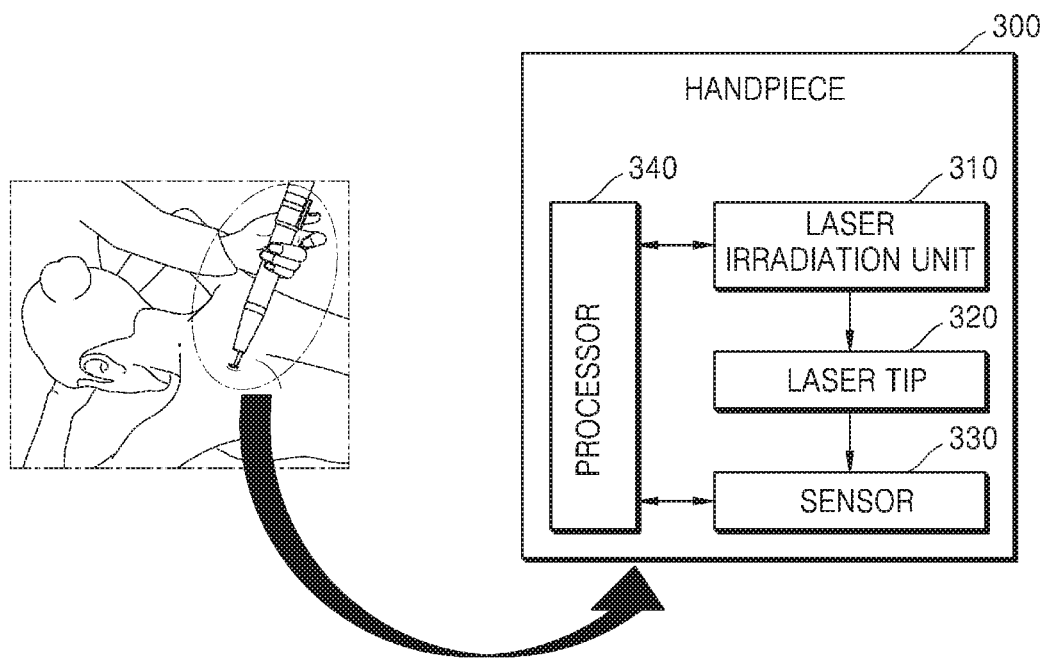
FIG. 3 is a block diagram illustrating the configuration of a handpiece according to an aspect.

FIG. 3 is a block diagram illustrating the configuration of a handpiece according to an aspect.

A handpiece 300 may include a laser irradiation unit 310, a laser tip 320, a sensor 330, and a processor 340. Not all of the components shown are essential. The handpiece 300 may be implemented by more components than the illustrated components, or the handpiece 300 may also be implemented by fewer components. The handpiece 300 of FIG. 3 may perform the same function as the handpiece 300 of FIG. 2. In addition, the handpiece 300 of FIG. 3 may further include a processor than the handpiece 300 of FIG. 2. The processor 340 of the handpiece 300 may control an operation of the handpiece 300 and the signal flow between internal components of the handpiece 300. In addition, the processor 340 of the handpiece 300 may transmit a signal or data obtained by the handpiece 300 to the body 200 of the medical laser device 100. Hereinafter, the components described above will be described.

The laser irradiation unit 340 may be connected to the body 200 that generates a laser, and may irradiate the subject with the laser. A laser of a first wavelength generated by the laser oscillation unit 220 of the body 200 may be provided to the laser irradiation unit 310. The laser irradiation unit 310 may convert the laser of the first wavelength into a laser of a second wavelength and may output the laser of the second wavelength. On the other hand, the laser oscillation unit 220 of the body 200 may include a medical Q-switching Nd:YAG laser that generates a wavelength in a band of 1064 nm. The laser of the second wavelength output by the laser oscillation unit 220 may be in a band from 2700 to 3000 nm. It will be understood by those skilled in the art that the range of the wavelength is just an example and aspects of the present disclosure are not limited thereto.

The laser tip 320 may be brought into contact with a predetermined surgical site of a subject so as to guide the laser. The laser tip 320 may press the inside of blood vessels within an irradiation region. For example, the laser tip 320 may be arranged along a longitudinal direction of the blood vessels inside the irradiation region and may press one side in the longitudinal direction of the blood vessels so that the blood vessels within the irradiation region may expand. In addition, the laser tip 320 may have a diagonal cross-sectional shape or a curved cross-sectional shape.

The sensor 330 may be installed in the laser tip 320 and may measure pressure applied to a predetermined surgical site by the laser tip 320. Here, the sensor 330 may be a film-type sensor and may be installed at an end of the laser tip 320. For example, the sensor 300 may be a pressure sensor made of a transparent thin-film material, and aspects of the present disclosure are not limited thereto. In addition, the sensor 330 may include a plurality of sub-sensors. The plurality of sub-sensors may be arranged and installed at an end of the laser tip 320 that is in contact with a predetermined surgical site.

The laser tip 320 may induce a tension with a predetermined size to the predetermined surgical site while pressing the predetermined surgical site. The plurality of sub-sensors may be brought into contact with the predetermined surgical site so as to measure the tension induced to the predetermined surgical site.

The processor 340 may check whether the measured pressure is within the pressure range set for the predetermined surgical site. The processor 340 may determine whether the pressure applied to the predetermined surgical site needs to be adjusted, according to the result of checking, and may perform control so that the guide signal for the laser tip 320 may be output.

For example, if it is checked that the measured pressure is out of the pressure range set for the predetermined surgical site, the processor 340 may generate a guide signal on the basis of a degree at which the measured pressure is out of the pressure range. The processor 340 may perform control so that the generated guide signal or guide information corresponding to the guide signal may be output.

In detail, if it is checked that the size of the measured pressure is less than the size of the minimum pressure in the set pressure range, the processor 340 may perform control so that a first sound signal may be output through a speaker (not shown) of the body 200. After the first sound signal is output, as the pressure measured at the predetermined surgical site approaches the set pressure range, the processor 340 may perform control so that the magnitude of the first sound signal may be gradually decreased and the first sound signal may be output through the speaker (not shown) of the body 200.

In addition, if it is checked that the size of the measured pressure is greater than the size of the maximum pressure in the set pressure range, the processor 340 may perform control so that a second sound signal may be output through the speaker (not shown) of the body 200. After the second sound signal is output, as the pressure measured at the predetermined surgical site is away from the set pressure range, the processor 340 may perform control so that the magnitude of the second sound signal may be gradually increased and the second sound signal may be output through the speaker (not shown) of the body 200.

In addition, the processor 340 may transmit a signal indicating that the measured pressure is out of the pressure range set for the predetermined surgical site, to the body 200 through a signal line. The body 200 may display a guide image for applying an optimal pressure by using a laser guide tip on the basis of the signal transmitted from the processor 340 of the handpiece 300.

In another example, if it is checked that the measured pressure is within the pressure range set for the predetermined surgical site, the processor 340 may perform monitoring so that the pressure within the set pressure range may be applied to the predetermined surgical site. That is, the processor 340 may induce the optimal pressure to be applied to the optimal pressure to the predetermined surgical site.

The handpiece 300 may induce the optimal pressure to be applied to the predetermined surgical site of the object by using the sensor 330 installed in the laser tip 320 so that the effect of treatment may be enhanced. In addition, if the pressure measured by the sensor 330 is out of the set predetermined surgical site, the handpiece 300 may generate a guide signal that induces the pressure applied by the laser tip 320 to have the pressure within the predetermined pressure range, and may perform control so that the generated guide signal may be output.

In addition, the handpiece 300 may perform control so that a laser beam may be irradiated to the predetermined surgical site within the predetermined pressure range so that the laser beam may be focused on the dermis.

Hereinafter, various operations or applications performed by the medical laser device 100, the body 200 or the handpiece 300 of the medical laser device 100 will be described. Even when any one of the processor 210 of the body 200, the laser oscillation unit 220, the display 230, the control panel 240, the memory 250, the laser irradiation unit 310, the laser tip 320, the sensor 330, and the processor 340 of the handpiece 300 is not specified, the contents that can be clearly understood and predicted by those skilled in the art to which embodiments pertain, will be understood with general implementations, and the range of right of the medical laser device 100, the body 200 or the handpiece 300 of the medical laser device 100 is not limited by the name or physical/logical structure of a specific configuration.

Figure 4:
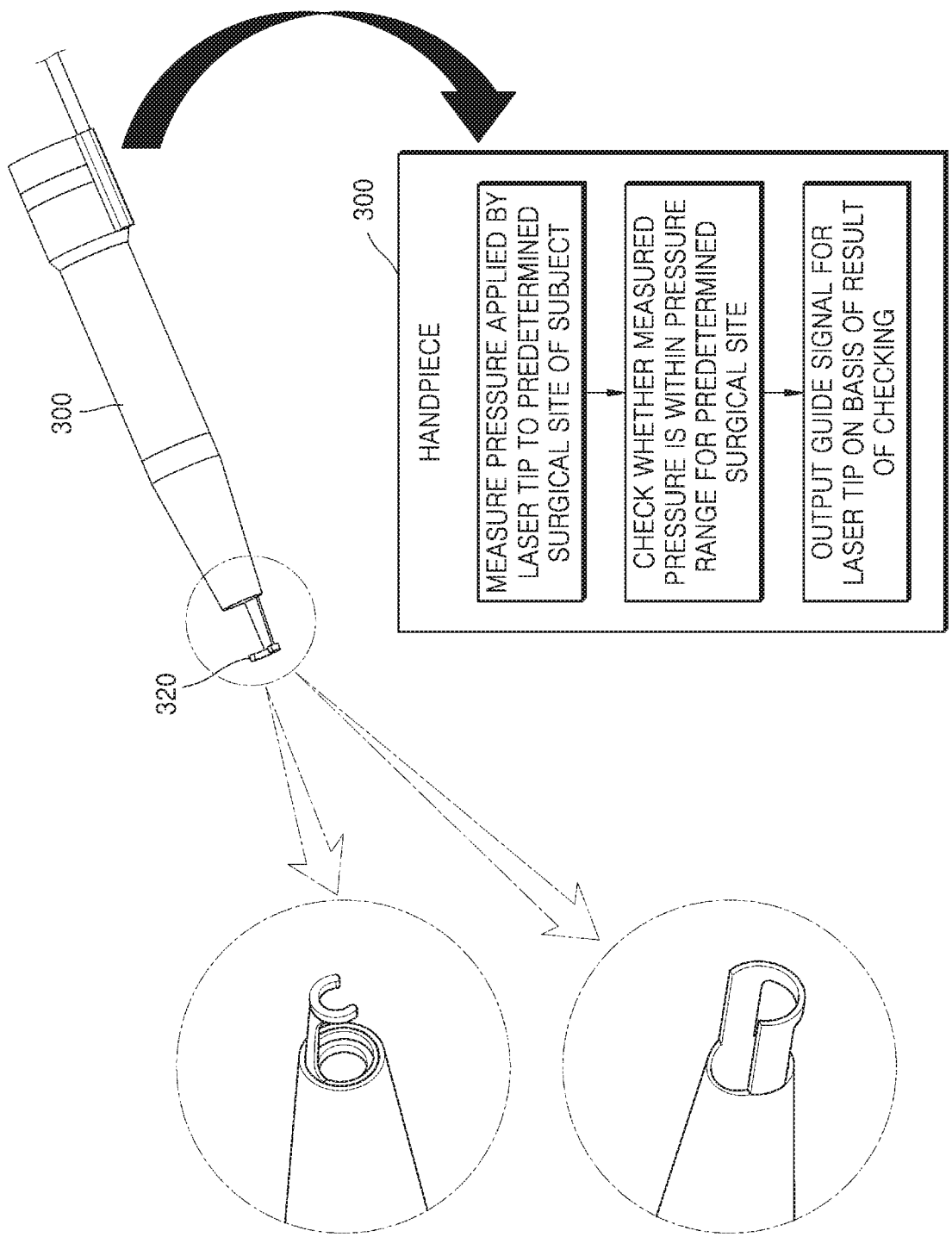
FIG. 4 is a view for explaining an operation in which a handpiece measures a pressure applied to a predetermined surgical site by using a sensor installed in a laser tip and outputs a guide signal for the laser tip according to the measured pressure.

FIG. 4 is a view for explaining an operation in which a handpiece measures a pressure applied to a predetermined surgical site by using a sensor installed in a laser tip, and outputs a guide signal for the laser tip according to the measured pressure.

The handpiece 300 may measure the pressure applied by the laser tip 320 to the predetermined surgical site through the sensor 330 installed in the laser tip. Here, the sensor 330 may be a film-type sensor and may be installed at an end of the laser tip 320. A description of the sensor 330 will be described in detail with reference to FIG. 5.

The handpiece 300 may check whether the pressure measured by the sensor 330 is within the pressure range set for the predetermined surgical site. As a result of checking, the handpiece 300 may perform control so that the guide signal for the laser tip 320 including information about adjusting of the pressure applied to the predetermined surgical site may be output.

For example, the handpiece 300 may generate a guide signal on the basis of a degree at which the measured pressure is out of the set pressure range, and may perform control so that the guide signal may be output.

In detail, if it is checked that the size of the measured pressure is less than the size of the minimum pressure within the set pressure range, the handpiece 300 may perform control so that a first sound signal may be output through a speaker (not shown) of the body 200 or a speaker (not shown) of the handpiece 300. After the first sound signal is output, as the pressure measured at the predetermined surgical site approaches the set pressure range, the handpiece 300 may perform control so that the magnitude of the first sound signal may be gradually decreased and the first sound signal may be output through the speaker (not shown) of the body 200 or the speaker (not shown) of the handpiece 300.

In addition, if it is checked that the size of the measured pressure is greater than the size of the maximum pressure within the set pressure range, the handpiece 300 may perform control so that a second sound signal may be output through the speaker (not shown) of the body 200 or the speaker (not shown) of the handpiece 300. After the second sound signal is output, as the pressure measured at the predetermined surgical site is away from the set pressure range, the handpiece 300 may perform control so that the magnitude of the second sound signal may be gradually increased and the second sound signal may be output through the speaker (not shown) of the body 200 or the speaker (not shown) of the handpiece 300.

Figure 5A:
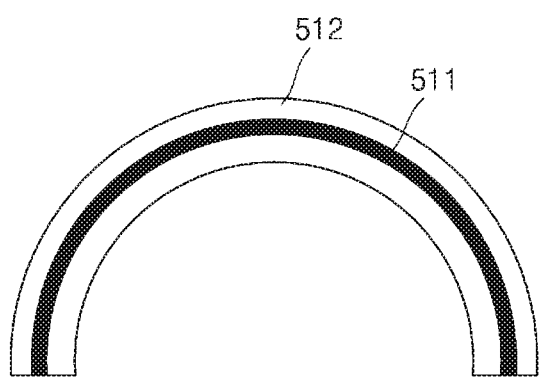
FIG. 5 is a view for explaining an example in which a sensor is installed in the laser tip, according to an aspect.
Figure 5B:
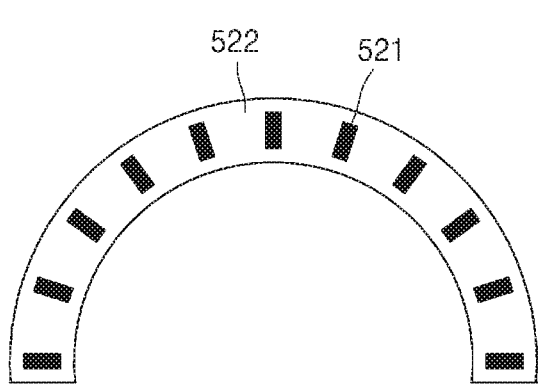

FIG. 5 is a view for explaining an example in which a sensor is installed in the laser tip, according to anaspect.

As shown in 510 of FIG. 5, the sensor 330 may be a film-type sensor. For example, the sensor may be a pressure sensor made of a transparent thin-film material, and aspects of the present disclosure are not limited thereto. For example, the pressure sensor may be an electrical pressure sensor, such as a strain gauge type, a capacitive type, a piezoelectric type, an inductance type, a semiconductor type FSR, and the like.

In addition, the sensor 330 may be installed at an end of the laser tip. In detail, the sensor may be installed at a border 512 at a horseshoe-shaped end of the laser tip and may be installed in the center within the border.

As shown in 520 of FIG. 5, the sensor 330 may include a plurality of sub-sensors. The plurality of sub-sensors may be arranged (521) at an end 522 of the laser tip that is in contact with the predetermined surgical site at predetermined intervals. Here, the narrower predetermined intervals decrease, the more precise the value of the pressure measured by the plurality of sub-sensors.

In addition, the sensor in 520 of FIG. 5 may be more suitable for measuring the pressure in a state in which a predetermined site is curved, than the sensor shown in 510 of FIG. 5.

FIG. 6 is a view for explaining a process of displaying guide information corresponding to a guide signal in a medical laser device when the pressure measured by the sensor is out of a set pressure range, according to an aspect.

Referring to 610 of FIG. 6, the user may use the medical laser device 100 so as to perform treatment on a predetermined site of the object. In this case, the user may hold the handpiece 300 of the medical laser device 100 so that the laser tip 320 within the handpiece 300 may be in contact with the predetermined site of the subject. The laser tip 320 may be brought into contact with the predetermined site so as to guide a laser. If the laser is irradiated onto the predetermined site in a state in which the laser tip 320 excessively presses the predetermined site or in a state in which the laser tip 320 is away from the predetermined site, the effect of treatment may be lowered. Thus, the laser tip 320 needs to be guided so that the optimal pressure may be applied to the predetermined site.

The medical laser device 100 may measure the pressure applied by the laser tip 320 to the predetermined surgical site through the sensor 330 installed in the laser tip 320. The medical laser device 100 may check whether the measured pressure is within in the pressure range set for the predetermined surgical site. As a result of checking, if it is checked that the measured pressure is out of the pressure range set for the predetermined surgical site, the medical laser device 100 may generate a guide signal on the basis of a degree at which the measured pressure is out of the pressure range, and may perform control so that the guide signal may be output. The medical laser device 100 may display a degree at which the measured pressure is out of the pressure range set for the predetermined surgical site, on the display 230 on the basis of the guide signal.

In detail, if it is checked that the size of the measured pressure is less than the size of the minimum pressure in the set pressure range, as shown in 620 of FIG. 6, the medical laser device 100 may display the pressure range set for the predetermined surgical site and may display the measured pressure in a region indicating less pressure than the minimum pressure in the pressure range. In addition, as shown in 630 of FIG. 6, the medical laser device 100 may display a guide phrase "please increase force applied to the laser tip 320 a little more" so as to guide the laser tip 320, so that the optimal pressure may be applied to the predetermined site. In addition, the medical laser device 100 may also output the guide phrase by voice.

In addition, if it is checked that the size of the measured pressure is greater than the size of the maximum pressure in the set pressure range, as shown in 640 of FIG. 6, the medial laser device 100 may display a pressure range set for the predetermined surgical site and may display the measured pressure in the region indicating a greater pressure than the maximum pressure in the pressure range. In addition, as shown in 650 of FIG. 6, the medical laser device 100 may display a guide phrase "please slightly reduce force applied to the laser tip 320" so as to guide the laser tip 320, so that the optimal pressure may be applied to the predetermined site. In addition, the medical laser device 100 may also output the guide phrase by voice.

FIG. 7 is a view for explaining a process of displaying guide information corresponding to a guide signal in a medical laser device when the pressure measured by the sensor is within a set pressure range, according to an aspect.

Referring to 710 of FIG. 7, the medical laser device 100 may measure the pressure applied by the laser tip 320 to the predetermined surgical site through the sensor 330 installed in the laser tip 320. The medical laser device 100 may check whether the measured pressure is within the pressure range set for the predetermined surgical site. As a result of checking, if it is checked that the measured pressure is within the set pressure range, the medical laser device 100 may generate a guide signal so that the optimal pressure may be continuously applied to the predetermined surgical site, and may perform control so that the guide signal may be output. The medical laser device 100 may display guide information corresponding to the guide signal.

As shown in 720 of FIG. 7, the medical laser device 100 may display the pressure range set for the predetermined surgical site and may display the pressure measured within the pressure range. In addition, as shown in 730 of FIG. 7, the medical laser device 100 may display a guide phrase "please keep force currently applied to a laser tip" so that the pressure applied to the predetermined surgical site may be kept, on the display 230. In addition, the medical laser device 100 may also output the guide phrase by voice.

Figure 8:
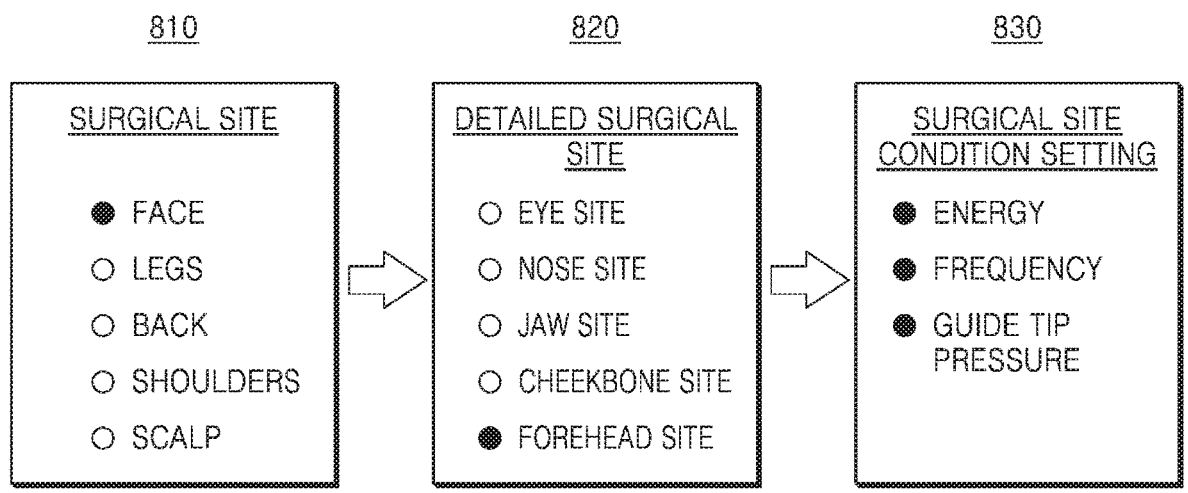
FIG. 8 is a view for describing a process in which a user selects a surgical site in a medical laser device and sets conditions of the medical laser device for the surgical site, according to an aspect.

FIG. 8 is a view for describing a process in which a user selects a surgical site in a medical laser device and sets conditions of the medical laser device for the surgical site, according to an aspect.

The medical laser device 100 may include a user interface that receives data for controlling the medical laser device 100 from the user. The medical laser device 100 may generate and output a user interface screen for receiving a predetermined command or data from the user. The user interface may be combined with the touch panel and implemented with a touch screen.

Referring to 810 of FIG. 8, the medical laser device 100 may display an execution screen for selecting a surgical site. In FIG. 8, only the face, legs, back, shoulders, and scalp are described as the surgical site but it will be understood by those skilled in the art to which the present disclosure pertains, that other sites may also be included.

Referring to 820 of FIG. 8, as the user selects the "face", the medical laser device 100 may display an execution screen for selecting a detailed surgical site with respect to the "face" site. The detailed surgical site with respect to the "face" site may include an eye site, a nose site, jaw site, a cheekbone site, and a forehead site, and aspects are not limited thereto.

Referring to 830 of FIG. 8, as the user selects the "forehead site", the medical laser device 100 may display an execution screen for setting "surgical site conditions". Even in the same face site, conditions to be set for treatment may be different according to the detailed site. For example, parameters for conditions to be set for treatment may include energy, frequency, and pressure applied by a guide tip to the skin, and it will be understood by those skilled in the art to which the present disclosure pertains, that other parameters may be included.

Figure 9:
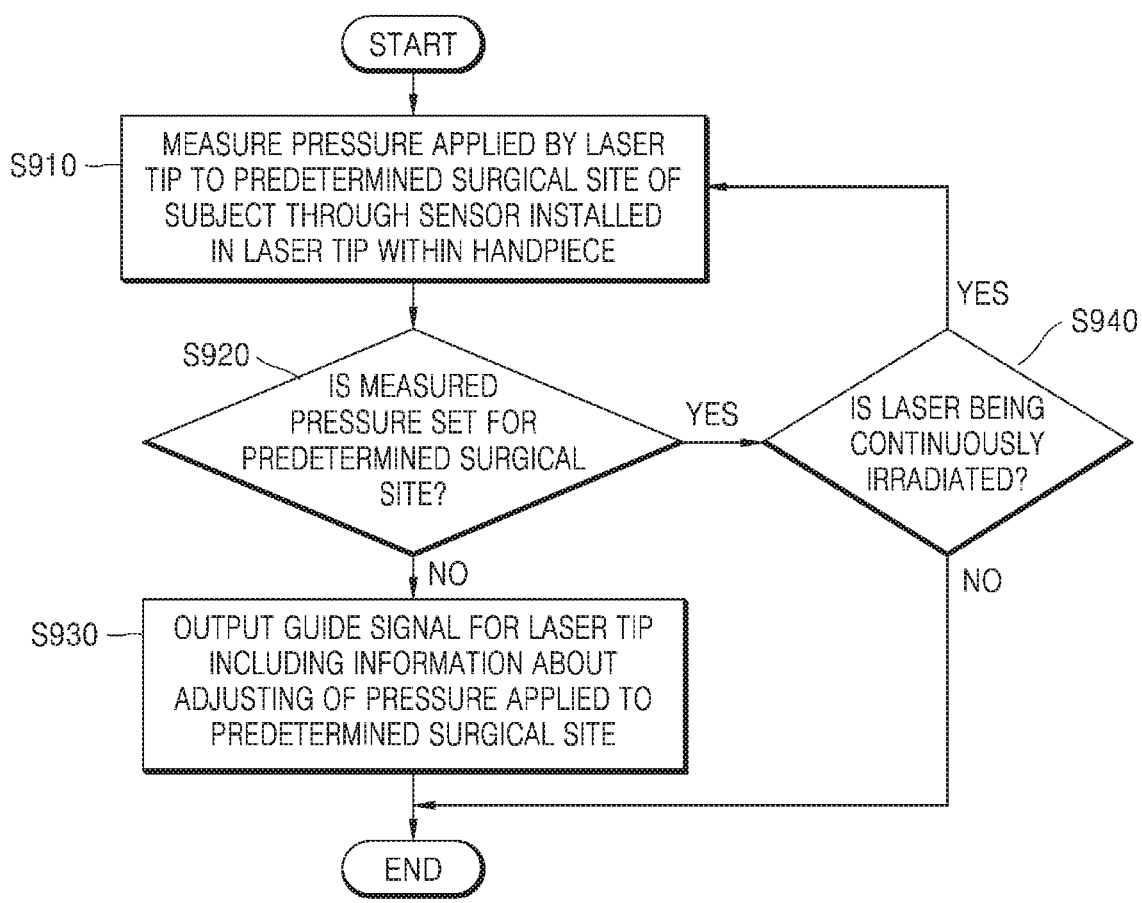
FIG. 9 is a flowchart illustrating a method of outputting a guide signal for a laser tip by using the pressure measured at a predetermined surgical site in a handpiece, according to an aspect.

FIG. 9 is a flowchart illustrating a method of outputting a guide signal for a laser tip by using the pressure measured at a predetermined surgical site in a handpiece, according to an aspect.

In Operation S910, the handpiece 300 may measure the pressure applied by the laser tip 320 to the predetermined surgical site through the sensor 330 installed in the laser tip 320.

In Operation S920, the handpiece 300 may check whether the pressure measured by the sensor 330 is within the pressure range set for the predetermined surgical site. If the measured pressure is out of the set pressure range, the handpiece 300 may operate according to Operation S930. Contrary to this, if the measured pressure is within the set pressure range, the handpiece 300 may operate according to Operation S940.

In Operation S930, the handpiece 300 may perform control so that the guide signal for the laser tip 320 including information about adjusting of the pressure applied to the predetermined surgical site may be output. For example, the handpiece 300 may generate a guide signal on the basis of a degree at which the measured pressure is out of the set pressure range, and may perform control so that the guide signal may be output.

In Operation S940, the handpiece 300 may check whether the laser is being continuously irradiated onto the laser irradiation unit 310 of the handpiece 300. When the laser is continuously irradiated, the handpiece 300 may go back to Operation S910 and may perform monitoring on the pressure applied to the predetermined surgical site in real-time so as to induce the optimal pressure to be applied to the predetermined surgical site. Contrary to this, when the laser is not continuously irradiated, the handpiece 300 may stop monitoring on the pressure applied to the predetermined surgical site.

On the other hand, in the above-described aspects, the handpiece 300 may be provided in the form of a computer program stored in a computer-readable storage medium so as to perform a method of outputting a guide signal for the laser tip 320 by using the pressure measured at the predetermined surgical site.

Figure 10:
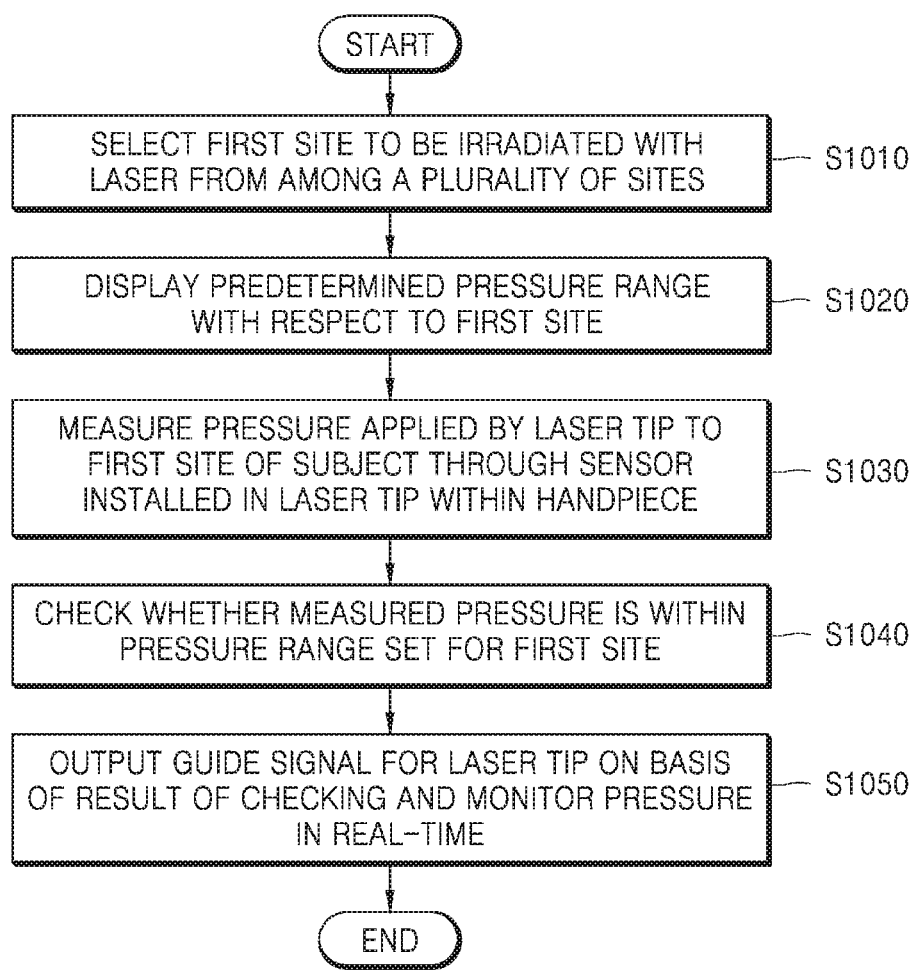
FIG. 10 is a flowchart illustrating a method of outputting a guide signal for a laser tip by using the pressure measured at a predetermined surgical site in a medical laser device, according to an embodiment.

FIG. 10 is a flowchart illustrating a method of outputting a guide signal for a laser tip by using the pressure measured at a predetermined surgical site in a medical laser device, according to an aspect.

In Operation S1010, the medical laser device 100 may receive an input for selecting a first site at which a laser is to be irradiated, from among a plurality of sites through the display 230 or the control panel 240.

In Operation S1020, the medical laser device 100 may display a predetermined pressure range with respect to the first site on the display 230. Here, the predetermined pressure range may be the range of an optimal pressure to be applied to the predetermined surgical site for laser treatment. The predetermined pressure range may be set differently for each of sites of the subject.

In Operation S1030, the medical laser device 100 may measure the pressure applied by the laser tip 320 to the first site of the subject through the sensor 330 installed in the laser tip 320 within the handpiece 300.

In Operation S1040, the medical laser device 100 may check whether the measured pressure is within the pressure range set for the first site.

In Operation S1050, the medial laser device 100 may output a guide signal for the laser tip 320 based on the result of checking. In addition, the medical laser device 100 may monitor the pressure measured by the sensor 330 so as to induce the optimal pressure to be applied to the first site.

On the other hand, in the above-described aspects, the medical laser device 100 may be provided in the form of a computer program stored in a computer-readable storage medium so as to perform a method of outputting the guide signal for the laser tip 320 by using the pressure measured at the predetermined surgical site.

As described above, although the aspects have been described by a limited aspect and the drawings, those skilled in the art can make various modifications and variations from the following description. For example, even if the described technologies are performed in a different order than the described method or/and components such as the described system, structure, device, and circuit, etc. are combined in a different form than the described method or may be replaced or substituted with other components or equivalents, appropriate results can be achieved.

Therefore, the scope of the present disclosure is defined not by the described aspect but by the appended claims and equivalents to the claims.

What is claimed is:
1. A medical handpiece comprising:
a laser irradiation unit connected to a body for generating a laser, so as to irradiate a subject with the laser;
a laser guide tip extending from one side of a distal end of the laser irradiation unit, the laser guide tip configured to contact a predetermined surgical site of the subject so as to guide the laser thereto;
a sensor including a plurality of sub-sensors arranged at a predetermined interval and installed in an end of the laser guide tip so as to measure pressure applied by the laser guide tip to the predetermined surgical site, wherein the plurality of sub-sensors are configured so as to contact the predetermined surgical site to measure a tension induced by medical handpiece manipulation via contact of the laser guide tip to the predetermined surgical site; and
a processor for checking whether the measured pressure is within the pressure range set for the predetermined surgical site, determining, according to the result of the checking, whether the pressure applied to the predetermined surgical site needs to be adjusted, and performing control such that a guide signal for the laser guide tip is output.

2. The medical handpiece of claim 1, wherein, in a case where it is checked that the measured pressure is out of the pressure range set for the predetermined surgical site, the processor generates a guide signal on the basis of a degree at which the measured pressure is out of the pressure range, and performs control so that the guide signal is output.

3. The medical handpiece of claim 2, wherein, in a case where it is checked that the size of the measured pressure is less than the size of a minimum pressure in the set pressure range, the processor performs control so that a first sound signal is output, and as the pressure measured at the predetermined surgical site approaches the set pressure range, the processor performs control so that a magnitude of the first sound signal is decreased and the first sound signal is output, and,
in a case where it is checked that the size of the measured pressure is greater than the size of a maximum pressure in the set pressure range, the processor performs control so that a second sound signal is output, and as the pressure measured at the predetermined surgical site is away from the set pressure range, the processor performs control so that a magnitude of the second sound signal is increased and the second sound signal is output.

4. The medical handpiece of claim 1, wherein the sensor comprises a film-type sensor.

5. A medical laser device comprising:
a body for generating a laser;
a handpiece connected to the body, so as to irradiate the laser;
a sensor including a plurality of sub-sensors arranged at a predetermined interval and installed in an end of a laser guide tip extending from one side of a distal end of the handpiece and measuring the pressure applied by the laser guide tip to a predetermined surgical site of a subject, wherein the plurality of sub-sensors are configured so as to contact the predetermined surgical site to measure a tension induced by handpiece manipulation via contact of the laser guide tip to the predetermined surgical site; and
a processor for checking whether the measured pressure is within the pressure range set for the predetermined surgical site, determining, according to the result of the checking, whether the pressure applied to the predetermined surgical site needs to be adjusted, and performing control such that a guide signal for the laser guide tip is output.

6. The medical laser device of claim 5, wherein, in a case where the measured pressure is out of a pressure range set for the predetermined surgical site, the processor generates a guide signal on the basis of a degree at which the measured pressure is out of the pressure range, and performs control so that the guide signal is output.

7. The medical laser device of claim 6, wherein, in a case where it is checked that the size of the measured pressure is less than the size of a minimum pressure in the set pressure range, the processor performs control so that a first sound signal is output, and as the pressure measured at the predetermined surgical site approaches the set pressure range, the processor performs control so that a magnitude of the first sound signal is decreased and the first sound signal is output, in a case where it is checked that the size of the measured pressure is greater than the size of a maximum pressure in the set pressure range, the processor performs control so that a second sound signal is output, and as the pressure measured at the predetermined surgical site is away from the set pressure range, the processor performs control so that a magnitude of the second sound signal is increased and the second sound signal is output.

8. The medical laser device of claim 5, further comprising a display for displaying an execution screen for controlling an operation of the medical laser device or an image related to the predetermined surgical site, wherein
the processor generates a guide signal for the laser guide tip on the basis of pressure information measured by the sensor and a pressure range set for the predetermined surgical site and performs control so that guide information corresponding to the guide signal for the laser guide tip is displayed on the display.

9. The medical laser device of claim 8, wherein, in a case where it is checked that the measured pressure is out of the pressure range set for the predetermined surgical site, the processor performs control so that a degree at which the measured pressure is out of the pressure range set for the predetermined surgical site, is displayed on the display on the basis of the guide signal.

10. The medical laser device of claim 8, further comprising memory for storing information in which a predetermined pressure range corresponding to the plurality of sites of the subject is set, for each of the plurality of sites of the subject, wherein
the display receives an input for selecting a first site from among the plurality of sites as a site to be irradiated with a laser beam, through an execution screen for controlling an operation of the medical laser device, and
the processor determines whether the pressure needs to be adjusted to the first site, on the basis of the pressure measured by the sensor, and performs control so that a guide signal for the laser guide tip is output.

11. The medical laser device of claim 5, wherein the sensor comprises a film-type sensor.

12. A computer-readable storage medium on which commands that can be executed by a program, are stored, comprising:
a first command for measuring the pressure applied by a laser guide tip to a predetermined surgical site of a subject through a sensor including a plurality of sub-sensors arranged at a predetermined interval and installed in an end of the laser guide tip extending from one side of a distal end of a handpiece, wherein the plurality of sub-sensors are configured so as to contact the predetermined surgical site to measure a tension induced by medical handpiece manipulation via contact of the laser guide tip to the predetermined surgical site;
a second command for checking whether the measured pressure is within a pressure range set for the predetermined surgical site; and
a third command for determining, according to the result of the checking, whether the pressure applied to the predetermined surgical site needs to be adjusted, and performing control so that a guide signal for the laser guide tip is output.

* * * * *